(12) United States Patent
Jones et al.

(10) Patent No.: US 8,899,114 B2
(45) Date of Patent: Dec. 2, 2014

(54) ENERGY INTENSITY TRANSFORMATION

(75) Inventors: Christopher M. Jones, Houston, TX (US); Michael T. Pelletier, Houston, TX (US); Robert Atkinson, Richmond, TX (US); Wei Zhang, Houston, TX (US); Li Gao, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 281 days.

(21) Appl. No.: 13/386,338

(22) PCT Filed: Jul. 30, 2009

(86) PCT No.: PCT/US2009/004401
§ 371 (c)(1),
(2), (4) Date: Mar. 21, 2012

(87) PCT Pub. No.: WO2011/014144
PCT Pub. Date: Feb. 3, 2011

(65) Prior Publication Data
US 2012/0167692 A1 Jul. 5, 2012

(51) Int. Cl.
*G01N 29/04* (2006.01)
*G01J 3/30* (2006.01)
*G01N 21/59* (2006.01)
*E21B 49/08* (2006.01)

(52) U.S. Cl.
CPC .............. *G01N 21/59* (2013.01); *E21B 49/08* (2013.01)
USPC ........................... 73/642; 73/646; 250/227.11

(58) Field of Classification Search
USPC ............... 73/645, 646, 642; 250/216, 227.11, 250/311, 390.01, 577
See application file for complete search history.

(56) References Cited

U.S. PATENT DOCUMENTS

| 3,576,521 | A | * | 4/1971 | Silverman | .................. 367/10 |
| 4,099,417 | A | * | 7/1978 | Shwartzman | .................. 73/606 |
| 4,648,713 | A | | 3/1987 | Borer et al. | |
| 4,786,171 | A | | 11/1988 | LeFebre et al. | |
| 4,955,001 | A | * | 9/1990 | Guigne | .................. 367/118 |

(Continued)

FOREIGN PATENT DOCUMENTS

| EP | 1203942 A1 | 5/2002 |
| WO | WO-2006/125470 A1 | 11/2006 |
| WO | WO-2011014144 A1 | 2/2011 |

OTHER PUBLICATIONS

"Australian Application Serial No. 2009350491, Subsequent Examiners Report mailed Jan. 7, 2013", 3 pgs.

(Continued)

*Primary Examiner* — Helen Kwok
(74) *Attorney, Agent, or Firm* — Schwegman Lundberg & Woessner, P.A.; Benjamin Fite

(57) ABSTRACT

Apparatus, systems, and methods may operate to receive incident energy within a chamber defining a first part of an interaction volume that attenuates the incident energy as a function of path length to provide attenuated energy. Additional activity may include simultaneously transforming the attenuated energy characterized by a substantially exponential intensity function into resultant energy characterized by a substantially polynomial intensity function. The transformation may be accomplished using an interacted energy transformation element that defines a second part of the interaction volume, the transformation element operating to intercept the attenuated energy along a plurality of path lengths. Other activity may include transmitting the resultant energy to a receiver. Additional apparatus, systems, and methods are disclosed.

20 Claims, 11 Drawing Sheets

(56) References Cited

U.S. PATENT DOCUMENTS

| | | | |
|---|---|---|---|
| 5,048,970 | A | 9/1991 | Milosevic et al. |
| 5,124,555 | A | 6/1992 | Hartl |
| 5,144,839 | A * | 9/1992 | Lochner .................. 73/609 |
| 5,168,367 | A | 12/1992 | O'Rourke et al. |
| 5,186,896 | A | 2/1993 | Bouchee et al. |
| 5,268,736 | A | 12/1993 | Prather |
| 5,303,036 | A | 4/1994 | McLachlan et al. |
| 5,557,103 | A | 9/1996 | Hughes et al. |
| 5,760,309 | A * | 6/1998 | Maltby et al. .................. 73/646 |
| 5,859,430 | A | 1/1999 | Mullins et al. |
| 6,176,323 | B1 | 1/2001 | Weirich et al. |
| 6,219,132 | B1 | 4/2001 | Scharlack et al. |
| 6,465,775 | B2 | 10/2002 | Mullins et al. |
| 6,553,175 | B2 | 4/2003 | Jaspan |
| 6,573,988 | B1 | 6/2003 | Thomsen et al. |
| 6,639,921 | B1 | 10/2003 | Fukumoto |
| 6,643,016 | B2 | 11/2003 | Garver et al. |
| 6,741,365 | B2 | 5/2004 | Curtis |
| 6,766,074 | B1 | 7/2004 | Dingel et al. |
| 7,095,012 | B2 | 8/2006 | Fujisawa et al. |
| 2004/0069942 | A1 | 4/2004 | Fujisawa et al. |
| 2004/0136645 | A1 | 7/2004 | Dingel et al. |
| 2004/0179194 | A1 | 9/2004 | Schmilovitch et al. |
| 2004/0246501 | A1 | 12/2004 | Curtis |
| 2007/0171414 | A1 | 7/2007 | Vannuffelen et al. |
| 2008/0087836 | A1 | 4/2008 | Knight et al. |
| 2009/0027678 | A1 | 1/2009 | Salerno et al. |
| 2009/0059332 | A1 | 3/2009 | DiFoggio et al. |

OTHER PUBLICATIONS

"European Application Serial No. 098478928, Office Action mailed Dec. 13, 2012", 1 pg.

"European Application Serial No. 09847892.8, Response filed Jun. 12, 2013 to European Search Report mailed Nov. 26, 2012", 13 pgs.

"Australian Application Serial No. 2009350491, Response filed Aug. 20, 2013 to Examiner's Report mailed Jan. 7, 2013", 25 pgs.

"Australian Application Serial No. 2009350491, First Examiner Report mailed Sep. 27, 2012", 3 pgs.

"Australian Application Serial No. 2009350491, Response filed Dec. 17, 2012 to First Examiner Report mailed Sep. 27, 2012", 8 pgs.

"European Application Serial No. 09847892.8, European Search Report mailed Nov. 26, 2012", 9 pgs.

Dong, L., et al., "High-sensitivity, large dynamic range, auto-calibration methane optical sensor using a short confocal Fabry-Perot cavity", *Sensors and Acutators B*, 127(2), (2007), 350-357.

Gong, R. K., et al., "A New Method to Improve the Precision of $SO_2$ Measurement in Atmosphere", *Journal of Physics*, 48(1), (2006), 1162-1166.

"International Application Serial No. PCT/US2009/04401, International Preliminary Report on Patentability mailed Jul. 28, 2011", 5 pgs.

"International Application Serial No. PCT/US2009/04401, Search Report mailed Sep. 22, 2009".

"International Application Serial No. PCT/US2009/04401, Written Opinion mailed Sep. 22, 2009".

Butt, G., et al., "A Variable Path Length Infrared Cell for Use at Elevated Temperatures", Applied Spectroscopy, 28(3), (May/Jun. 1974), 282-283.

Choat, T., et al., "Variable path length flow-through cell for spectrophotometry", Analytical Chemistry, 58(12), (Oct. 1986), 2570-2571.

Flowers, P. A., et al., "Variable Path Length Transmittance Cell for Ultraviolet, Visible, and Infrared Spectroscopy and Spectroelectrochemistry", Analytical Chemistry, 68(1), (Jan. 1, 1996), 199-202.

Gordon, R. R., et al., "Variable Path-Length Cell for the Measurement of the Absorption of Liquids in the Infra-Red Region of the Spectrum", Journal of Scientific Instruments, vol. 22, (Jan. 1945), 12-14.

Le Doucen, R., et al., "Variable path-length, low-temperature cells for absorption spectroscopy", J. Phys. E: Sci. Instrum., 18, (1985), 199-200.

"Australian Application Serial No. 2014200024, First Examiner Report mailed Jun. 11, 2014", 3 pgs.

* cited by examiner

ENERGY INTENSITY TRANSFORMATION

RELATED APPLICATIONS

This application is a U.S. National Stage Filing under 35 U.S.C. 371 from International Application No. PCT/US2009/004401, filed on Jul. 30, 2009, and published as WO 2011/014144 A1 on Feb. 3, 2011; which application and publication are incorporated herein by reference in their entirety.

BACKGROUND INFORMATION

Spectroscopic analysis makes use of a change in the properties of energy, such as light, after it interacts with a material sample. For example, the property of light most often correlated to a property of the sample is the intensity of the light. According to the Beer-Lambert law, the intensity of light transmitted through a samples varies exponentially with respect to the absorptivity of the sample (usually expressed as molar absorptivity or molecular absorptivity), the path length through which the light is transmitted, and the concentration of the absorbing species in the sample such that $I(\lambda)/I_0(\lambda) = \exp(L*E(\lambda)*C(\text{molecule specific}))$, where $I$ and $I_0$ represent the intensity before and after entering the sample, respectively, and where L is the optical path length, $E(\lambda)$ is the absorptivity, and C is the concentration of the sample.

Due to the exponential relationship, this law is often expressed in logarithmic form as $\log(I/I_0)=\text{LEC}$ (a wavelength and molecule specific form), or $-\text{Log}(I/I_0)=\text{Log}(I_0/I)=A$, where A is the adsorption, or $\text{Log}(1/I)=$optical density. For adsorption, it is assumed that the attenuation is due entirely to the absorption of photons by molecular species, whereas the optical density (OD) formulation does not make this assumption. Attenuation due to scattering may also cause a reduced intensity of transmitted light, however this relationship is also logarithmic and therefore the functional form of the Beer-Lambert law continues generally to be effective.

Thus, the Beer-Lambert law can serve to relate sample absorption to a chemical or physical-chemical property (physical properties that correlate with chemical properties) of the sample. However, it should be noted that while the law is founded on first principles and operates over a large range of E*C values, most analysis instruments do not. That is, to increase their dynamic range, different optical path lengths (L) are used to optimize response. These lengths are typically obtained by physically adjusting some arrangement of analyzer parts over a specific range, to change the path length of light transmitted through a sample. In addition, for high values of E*C, the law breaks down. Nonlinear calibration curves to extend analyzer dynamic range in these situations may be used.

DETAILED DESCRIPTION

Figure 1:
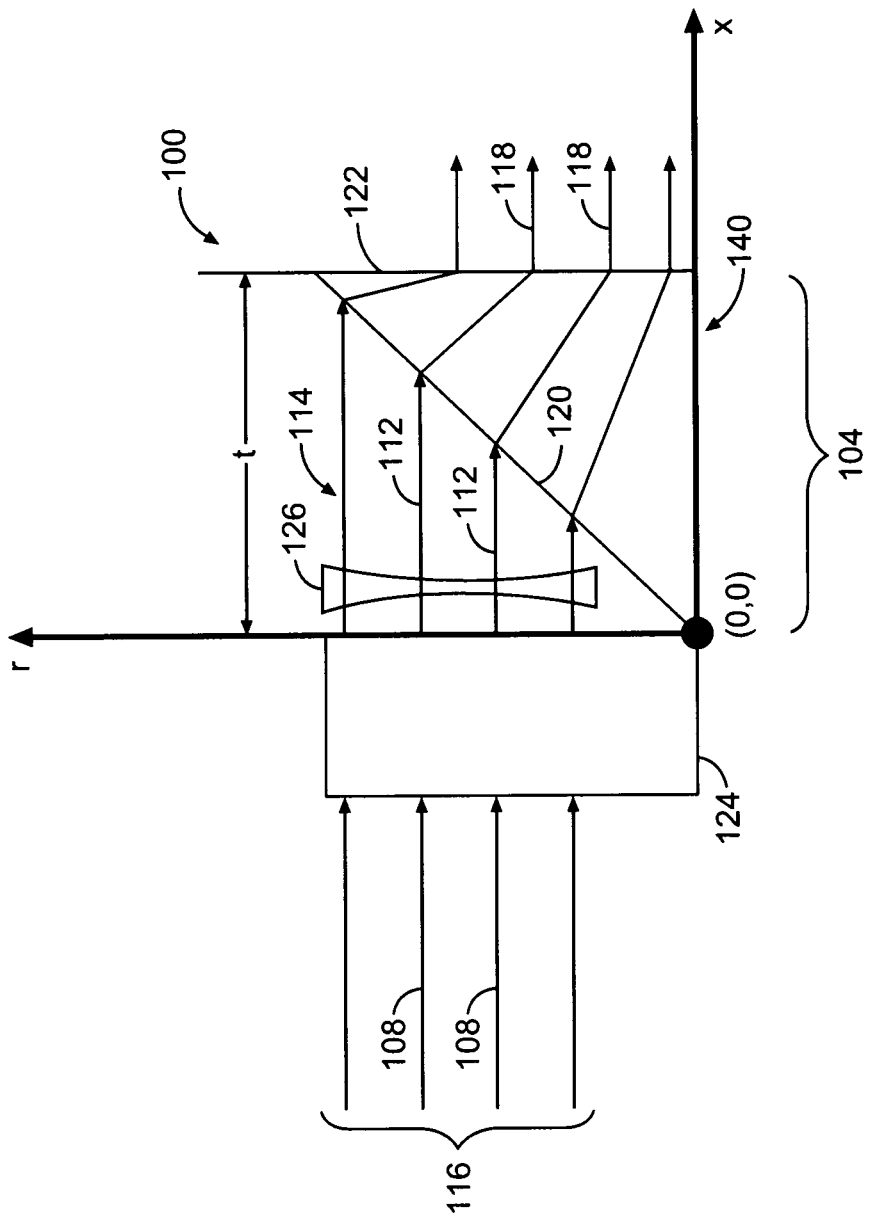
FIG. 1 illustrates a side, cut-away view of apparatus according to various embodiments of the invention.

The difficulty of performing spectroscopic analysis noted above may be compounded when such is attempted in a down hole environment. For example, the optical density of oils varies over many orders of magnitude such that no single fixed path length is optimal for all conditions. The path length minimum and maximum distances are sometimes limited in down hole applications due to temperature variations, and flow considerations (e.g., leading to plugging, or trapped volumes). The optical density of oils as a function of wavelength varies significantly, such that even for a single oil no single fixed path length is optimal for all wavelengths.

Further, most detector sensitivities are reduced at high temperature, such that the linear response range of a detector is greatly reduced in a down hole environment. The limit of detection of most detectors is compromised as a function of temperature such that more total transmittance is required for threshold operation.

It should be noted that many of these problems with the art are not unique to the oil industry. That is, they are common to most spectroscopic and photometric analysis designs, especially those used for industrial on line monitoring systems.

To solve some of these problems, it should be noted that in general, the effective path length of a multiple distance cell with two sets of two parallel windows is not the average of the two path lengths. From Beer's law: $I1=I_0*\exp(EL_1C)$, $I2=I_0*\exp(EL_2C)$, and $(I1/2+I2/2)=I_0*\exp(ELC)$, where L is the effective path length of the two individual path lengths. Therefore, $\ln[(I1+I2)/(2*I_0)]/EC=L$. However in terms of the original path lengths, $L=1-\ln(2)/EC+\ln[\exp(L1)+\exp(L2)]/EC$.

Some characteristics of the result can be noted:

L is the geometric mean of the individual path lengths;

E*C weights the geometric mean L such that for higher optical densities (i.e., when E*C is large), L is small, and for small optical densities (e.g., when E*C is small), L is large; and for the general case where $L(i)=f(x)$, the exponential mean can be combined in the integral such that $\int I(0, s) \exp[f(x)]$, where s is the final varied path length.

This suggests that there should be some function describing the point path length as a function of the window position "x" in which 1/T (where T is the total transmission as the sum of I(x)) is proportional to EC. Intuitively, from dimensional analysis, the two-dimensional path length cross section curve should have a conjugate logarithmic surface, and it is suggested that this surface takes the form of $1-\ln(x)$. An axisymmetric surface of the shape $$x = -\frac{1}{a}\text{Log}\left(\frac{r}{b}\right)$$

can be used as a generic example, where x is the optical path length and r is the distance from the revolving axis, and where a, b are two arbitrary positive constants. It may also be observed that $10^{-\alpha t}$ is negligibly small, which has physical meaning in that the tail part of the gap between two surfaces that bound the sample would not make any significant contribution. The boundary conditions can then be defined as: $x=t$ when $r=b \cdot 10^{-\alpha t}$ and $x=0$ when $r=b$.

In three-dimensional cylindrical coordinates, the outgoing intensity can be expressed as an integral over two coordinates r and θ:

$$I_{out} = \frac{\int_0^{2\pi} d\theta \int_{b \cdot 10^{-at}}^{b} I_{in} e^{-\alpha x} r \, dr}{\int_0^{2\pi} d\theta \int_{b \cdot 10^{-at}}^{b} r \, dr} =$$

$$\frac{2\pi \int_{b \cdot 10^{-at}}^{b} I_{in} e^{-\alpha x} r \, dr}{\pi b^2} = \frac{2}{b^2} \int_{b \cdot 10^{-at}}^{b} I_{in} e^{-\alpha x} r \, dr$$

The integral of the above equation can be evaluated as:

$$\frac{2}{b^2} \int_{b \cdot 10^{-at}}^{b} I_{in} e^{-\alpha x} r \, dr = \frac{2 I_{in}}{b^2} \int_{b \cdot 10^{-at}}^{b} e^{-\alpha \left(-\frac{1}{a} Log\left(\frac{r}{b}\right)\right)} r \, dr$$

$$= \frac{2 I_{in}}{b^2} \int_{b \cdot 10^{-at}}^{b} e^{\frac{\alpha}{a} Log\left(\frac{r}{b}\right)} r \, dr$$

$$= \frac{2 I_{in}}{b^2} \int_{b \cdot 10^{-at}}^{b} \left(\frac{r}{b}\right)^{\frac{\alpha}{a}} r \, dr$$

$$= \frac{2 I_{in}}{b^2} \int_{b \cdot 10^{-at}}^{b} \frac{r^{\frac{\alpha}{a}+1}}{b^{\frac{\alpha}{a}}} \, dr$$

$$= \frac{2 I_{in}}{b^{2+\frac{\alpha}{a}}} \int_{b \cdot 10^{-at}}^{b} r^{\frac{\alpha}{a}+1} \, dr$$

$$= \frac{2 I_{in}}{b^{2+\frac{\alpha}{a}} \left(\frac{\alpha}{a}+2\right)} r^{\frac{\alpha}{a}+2} \Big|_{b \cdot 10^{-at}}^{b}$$

$$= \frac{2 I_{in}}{b^{2+\frac{\alpha}{a}} \left(\frac{\alpha}{a}+2\right)} \left(b^{\frac{\alpha}{a}+2} - (b \cdot 10^{-at})^{\frac{\alpha}{a}+2}\right)$$

$$= \frac{2 I_{in}}{b^{2+\frac{\alpha}{a}} \left(\frac{\alpha}{a}+2\right)} \left(b^{\frac{\alpha}{a}+2} - b^{\frac{\alpha}{a}+2} \cdot 10^{-at\left(\frac{\alpha}{a}+2\right)}\right)$$

$$= \frac{2 I_{in}}{b^{2+\frac{\alpha}{a}} \left(\frac{\alpha}{a}+2\right)} \left(b^{\frac{\alpha}{a}+2} - b^{\frac{\alpha}{a}+2} \cdot 10^{-at-2at}\right)$$

$$= \frac{2 I_{in}}{\left(\frac{\alpha}{a}+2\right)}$$

This result shows:

$$\frac{I_{out}}{I_{in}} = \frac{2}{\left(\frac{\alpha}{a}+2\right)} \text{ or } \frac{I_{in}}{I_{out}} = \frac{\left(\frac{\alpha}{a}+2\right)}{2} = 1 + \frac{\alpha}{2a}, \quad [1]$$

where a is the absorption coefficient.

FIG. 1 illustrates a side, cut-away view of apparatus 100 according to various embodiments of the invention. Here it can be seen that the incident energy 108 enters a window 124 that, along with an interacted energy transformation element (IETE) 140, defines part of an interaction volume 114. In many embodiments, a material sample is disposed within the interaction volume 114, which is further defined by an inner surface of chamber (e.g., see chamber 290 in FIG. 2). The physical meaning of equation [1] is that transmission of energy through the IETE 140 now has a linear relationship with the absorption coefficient of material disposed within the interaction volume 114, rather than an exponential one. Therefore, the dynamic performance requirements for an analyzer that makes use of this type of IETE 140 are significantly reduced, which can be quite advantageous. It can also be shown that in the high optical density case (e.g., large EC), the shape of the cross section 104 for an energy transformation apparatus 100 approaches a linear wedge, with r on the vertical axis and x on the horizontal axis. This type of device is relatively easy to construct.

Expressing the Beer-Lambert law in the form $$\frac{I}{I_0} = e^{-\alpha t},$$

the total out-going density leaving the gap can be written:

$$I_{out,total} = \int_0^\tau \frac{I_{in,total}}{t} e^{-\alpha x} \, dr =$$

$$\int_0^\tau \frac{I_{in,total}}{t} e^{-\alpha r} \, dr = \frac{I_{in,total}}{t} \frac{1}{-\alpha} e^{-\alpha x} \Big|_0^t = I_{in,total} \frac{1-e^{-\alpha t}}{\alpha t}$$

with the understanding that x=r along the integration path. Therefore:

$$\frac{I_{out,total}}{I_{in,total}} = \frac{1-e^{-\alpha t}}{\alpha t}.$$

Taking the limits when αt is very small or very large:

$$\lim_{\alpha t \to 0} \frac{I_{out,total}}{I_{in,total}} = \frac{1-(1-\alpha t)}{\alpha t} = 1$$

and $$\lim_{\alpha t \to \infty} \frac{I_{out,total}}{I_{in,total}} = \frac{1}{\alpha t}.$$

Many practical considerations must be taken into account when constructing a real surface, such as the geometric configuration of the entire optical axis, collimation (or lack thereof) for the energy source, beam profile, chromatic dispersion, stability over temperature, scattering, part machining and reproducibility, dynamic range of the detector, dispersion, nonlinear deviation, and critical angles. For all these reasons, the entrance surface 120 of the IETE 140 realized in practice may deviate from the ideal surface or the linear cross section, which has a curve conforming to 1−ln(x).

If I/I₀=exp(ELC) and L=f(x), then I/I₀=exp(f(x)EC) and 1/I₀*I=exp(f(x)EC). It follows that int|1/I₀Iydy=int|exp(f(x)EC)dx. Thus, 1/I₀*T=int|exp(f(x))*exp(EC)dx, where T is the total transmission across the functional surface, 1/I0*T=exp(EC)*int|exp(f(x))dx, and 1/I₀*T=exp(EC)*exp(f(x))/f(x)', or the inverse, I₀*1/T=exp(−EC)*exp(−f(x))*f(x)'.

This final equation may be used in the numeric simulation of components as a performance metric for f(x), which can be modeled by a polynomial of order n, a polynomial spline of order n and window m, or some other appropriate generic curve form in which the coefficients can be optimized. It should also be noted that although f(x) generates a substantially smooth, continuous curve, the curve may be reflected, inverted, or rotated about axes of symmetry. In addition, for practical machined surfaces, the physical construct may be realized as localized linear approximations of the curve, or stepped approximations of the curve that is selected by the designer of the IETE 140. The surface form of the curve may be adjusted for various transmission spot shapes, and inhomogeneous spot intensity patterns.

It should be noted that in some applications, having T linear with respect to E*C may be more desirable than having 1/T being linear with respect to E*C. Although there is no ideal solution for T to be linear with respect to EC, a transform surface may be found in which T is approximately linear with respect to EC over the effective dynamic range of interest.

Figure 2:
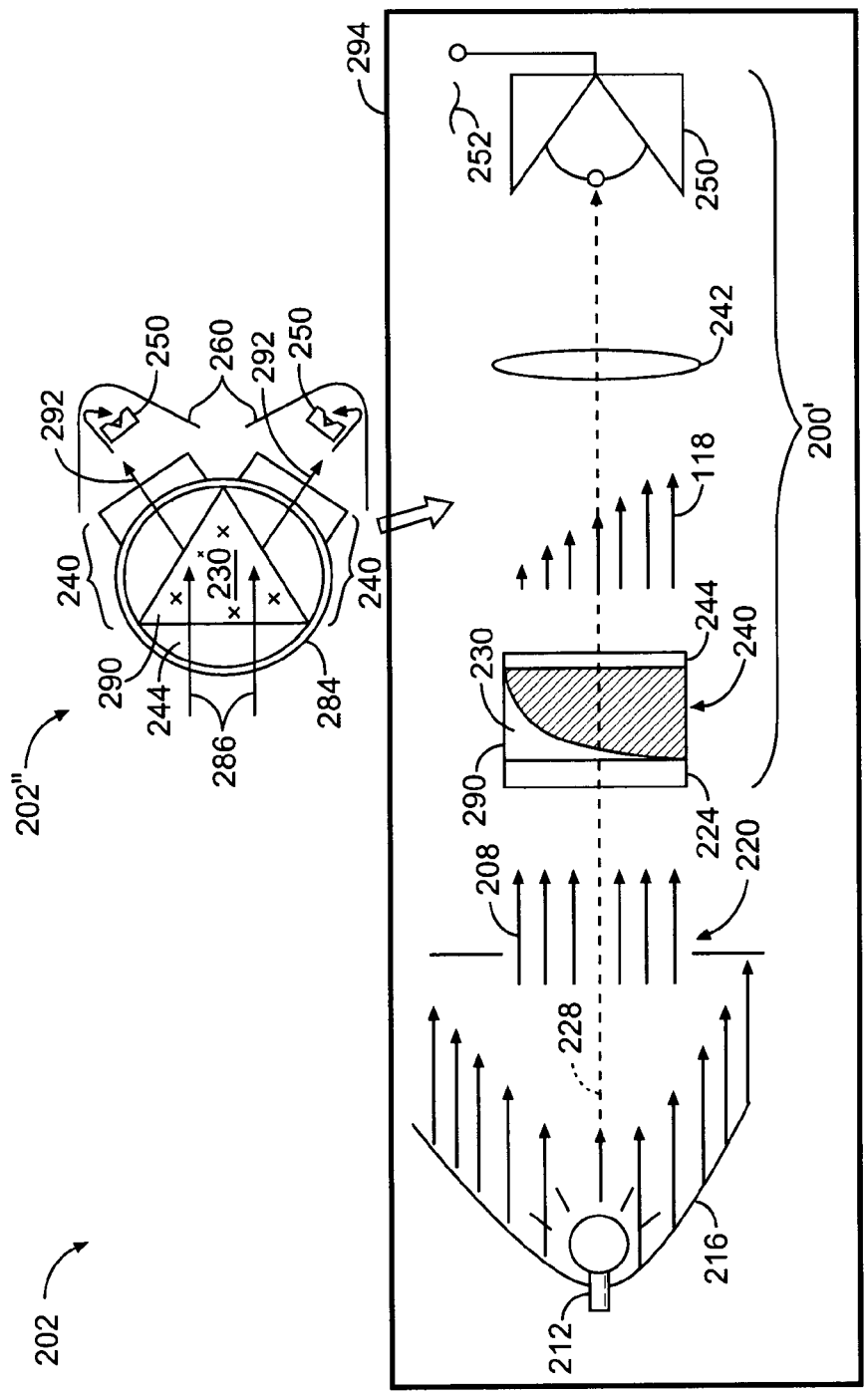
FIG. 2 illustrates a system block diagram according to various embodiments of the invention.

FIG. 2 illustrates a system 202 block diagram according to various embodiments of the invention. In this case, the system 202 comprises a generalized conceptual layout for a photometric analyzer using a variable path length cell that has no moving parts in the apparatus 200.

In this embodiment, light energy 208 from an energy source 212 is collimated with a parabolic reflector 216. A slit 220 captures the bulk of the collimated portion of the light energy 208, which passes through a window 224 normal to the optical axis 228 to reduce refraction.

The light energy 208 passes through a material sample 230 within a chamber 290 to encode the optical domain with molecular, chemical, and physical-chemical sample information. The light energy 208 then impinges on an IETE 240 to provide an integrated light intensity for which the transmittance or inverse transmittance (depending on the element design) is substantially linear with respect to sample absorption. In some embodiments, the IETE 240 provides a basis function for a representative oil. The light path may be corrected to a collimated path via back end optics 242, which may be incorporated into the back window 244, or separated into an individual optic or optics, as shown. The light energy 208 is then detected using a receiver 250 and a signal 252 from the receiver 250 may be provided that is proportional to a calibrated property.

Many different types of receivers 250 can be used. For example, the receiver 250 may comprise any type of sensor that responds to energy along the electromagnetic spectrum, the energy having a wavelength of approximately $10^{-1}$ m to $10^{-12}$ m. This includes charge-coupled device (CCD) sensors, liquid crystal diode (LCD) elements, spectrometers, photomultipliers, and others.

While FIG. 2 is shown using a photometric analysis setup (to process light energy 208), the principles described herein generally apply to spectroscopic analysis and other kinds of energy as well. Thus, when the term "light energy" is used herein, this has been done solely as a matter of convenience. Any type of incident energy (e.g., energy 108 in FIG. 1) may be substituted for the term light energy 208, and the various embodiments are not to be so limited. In addition, while the apparatus 200 is shown without moving parts in FIG. 2, it is to be noted that some embodiments make use of a movable IETE 240 that provides multiple sets of plural path lengths, further increasing the useful dynamic range of the total system 202.

Figure 3:
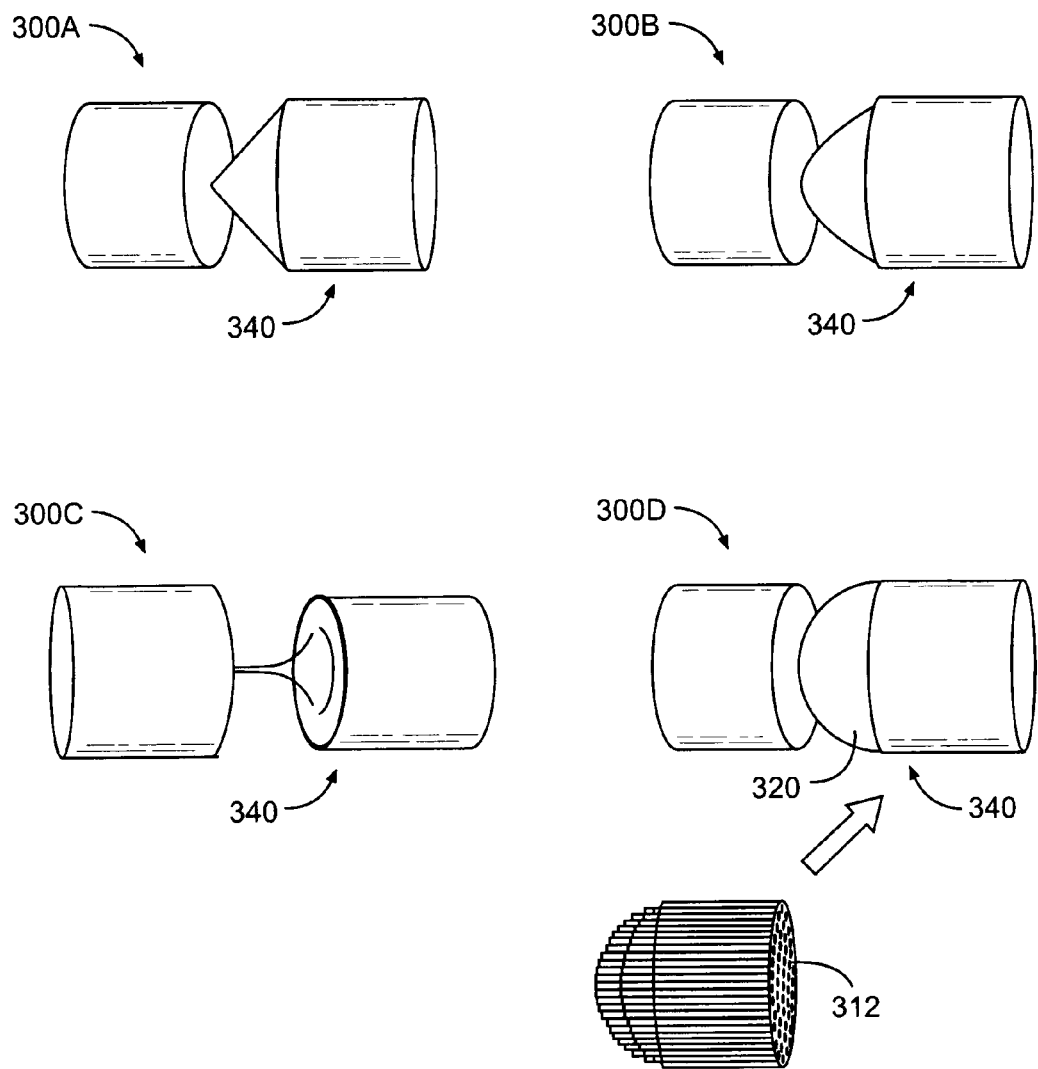
FIG. 3 illustrates rendered views of apparatus according to various embodiments of the invention.

FIG. 3 illustrates rendered views of apparatus 300 according to various embodiments of the invention. The apparatus 300 is similar to or identical to the apparatus 100, 200 of FIGS. 1, 2, respectively.

Simulations have shown that, for an idealized surface, 1/T (total transmittance) is substantially linearly proportional to the optical density of oil (as a sample material). A fixed-gap transformer with an average gap distance of 1.4 mm was able to reduce/transform over five orders of magnitude in transmittance variation to less than two orders of magnitude at the receiver (well within the range of commercially available high-temperature detectors). The logarithmic transform thus can serve to significantly transform the dynamic range of sample measurements and extend the bands of differing optical densities, while relaxing the range requirements at the receiver. In some embodiments, reduced sensitivity can be traded for increased dynamic range. If desired, the idealized surface may be tailored to provide a specific sensitivity over a specific dynamic range, so that for example, one could use a full two orders of magnitude in receiver performance over a selected range of oil optical densities (e.g., optical density (OD) of 1 to 8), instead of one order of magnitude in receiver performance for oil having an OD of 1 to 32.

In some cases, the idealized surface may not actually be easy to build. For example, a linear wedge transformation element (see the cross-section 104 of apparatus 100 in FIG. 1, realized as a linear cone element 340 of apparatus 300A in FIG. 3) can be easier to manufacture than a parabolic surface, shown as element 340 of apparatus 300B, or the logarithmic surface element 340 of the apparatus 300C. The linear cone of apparatus 300A can provide a logarithmic transform of 1/T over a relatively large optical density dynamic range. For example, in simulations using oil and an average path length of 5 mm, the response was substantially linear over OD values of 0.5 to 32.

A spherical transformation element 340, shown as part of the apparatus 300D, also presents a useful option. The advantages of a sphere include availability and ruggedness. The spherical transform is linear over a more narrow range than the wedge, however the total light throughput is greater, with improved sensitivity over a given dynamic range. For any of the elements 340 shown in FIG. 3, a stepped approximation may be used. For example, the spherical element 340 in the apparatus 300D may be approximated by a bundle of optical fibers 312. That is, the surface 320 of the transformation element 340 may be approximated by line segments, or stepped surfaces, as desired.

The possibilities for designing the surface 320 of the transformation element 340 are numerous. For example, the surface 320 may be contoured to minimize plugging due to small particles, or to provide representative flow. (perhaps including upstream modifications). The surface 320 may be shaped to account for un-collimated light due to scattering or imperfect initial collimation.

Using an iris or shutter, one may perform slope spectroscopy. Note that $I_0$ may be extrapolated in this case and slope spectroscopy is inherently robust in the face of path length changes. An aspheric back end may be mounted or molded to the window at the rear of the element 340 to correct for chromatic dispersion and collimation loss from a non parallel second window interface.

In some embodiments, a parabolic back reflector (e.g., see FIG. 2, elements 260) may collect light back to a single focal point if the loss of collimation is not great. In some embodiments, the surface 320 may be discontinuous with respect to a curve, with the total combined surface area having a histogram equal to that of a selected curve. For example, individual fibers may terminate at different lengths within a flow cell in random positions so long as the total number of fibers at a given distance approximates the shape of the curve desired. This arrangement might have advantages with respect to representative sampling. In some embodiments, the optical axis may be parallel to flow as opposed to perpendicular to flow, or indeed, at any arbitrary solid angle with respect to the flow axis Returning now to FIG. 2, an alternate embodiment of the apparatus 200 can be seen. The apparatus 200" can be used in lieu of the apparatus 200' shown in the path of the energy 208. In this case, the apparatus 200" is used with a flow of sample material 230 that moves into the drawing, and the parabolic reflectors 260 capture collimated light. Off-axis parabolic reflectors 260 could be used as well. The internal cylindrical chords create an equilateral triangular prism cavity, or chamber 290, in the center of the fluid flow.

Other geometric configurations could be used to fill the tube 284 to create a variety of geometric patterns for the chamber 290. If the window 244 material is made so as to have a common index of refraction with the tube 284 material (or if made of the same material), then the various parts 286 of the incident energy see no transition between window faces. If the chamber 290 is made of sapphire, then over the normal index of refraction changes for oils (e.g., about 1.2 to 1.6) the transformed energy beam will "walk" about 15 degrees away from the perpendicular. On or off-axis parabolic reflectors 260 can be used to compensate for this movement of the beams 292.

To test the concepts described, a basic oval wedge transformation element 240 was created by grinding the end of a fiber rod of BK7 material to a 22.5 degree angle. The light along the optical axis entered with less than a 3% divergence through a circular spot which cast an oval image on the fiber rod at the distal end of the optical gap. The fiber rod was ground in planar fashion to approximately 0.7 mm out of the spot to be flush with a sapphire rod window through which the collimated incident light illuminated the sample proximate to the oval wedge. The flush portion of the light had a gap of about 0 mm and the back end had a gap of 0.86 mm for an average gap of 0.48 mm. A planer window was set using the same sapphire rod and a different BK7 fiber rod that had a planer gap of 0.5 mm for comparison.

The optical density of crude oil at 550 nm was calculated for high dilutions of the fluid in toluene (which is primarily transparent at 550 nm) to an undiluted value. The expected optical density of the fluid was then calculated as a function of the dilution factor of the crude oil in toluene. A high degree of linearity was observed for the expected OD versus the observed OD, up to an OD of about 2.7 and a slight deviation up to an OD of about 600 for the planer gap. It should be noted that the linearity observed was for a gap of 0.5 mm, and the cutoff would have been lower for a 1 mm gap. The theoretical shape of an oval wedge with 22.5 degree angle does not approach a line as does a planer wedge. Rather, it approaches a parabola. When the actual response of the oval wedge is compared to the theoretical response, a good degree of linearity over the entire range was achieved, suggesting that the response function can be tuned to linearity with the proper shape. This test case implies that the linear dynamic range can be tuned as well. When the actual response is corrected for the parabolic behavior a by taking the square root of 1/T, a good degree of linearity is achieved for high optical densities.

Although the same degree of linearity was not observed for the variable path length case, it should be noted that the dynamic range of 1/T was observed over an expected OD of about 1 to 60. The reduced linearity may have been due to low machining tolerances, deviation of the sample with respect to the Beer-Lambert law at high OD, the fact that an oval wedge is not strictly a linear transform, a change in the gain of the detector at an expected optical density of 20, and multiple scattering from asphaltenes at high concentrations of oil. However, there was a good degree of linearity over an OD of about 1 to 14, which is still more than double the dynamic range provided by a parallel gap, albeit with a reduced signal to noise ratio. The experimental data results discussed above can be seen in FIGS. 8-14.

Thus, many practical embodiments may be realized. For example, referring now to FIGS. 1-3, it can be seen that an apparatus 100, 200, 300 may comprise a chamber 290 to define a first part of an interaction volume 114 that attenuates incident energy 108 as a function of path length t to provide attenuated energy 112 after the incident energy 108 has traveled through the interaction volume 114 along a plurality of paths 116. That is, there is usually no single length through the material sample 230 in which interaction with the attenuated energy 112 takes place; interaction occurs along a plurality of paths 116 having different lengths.

The apparatus 100, 200, 300 further comprises an IETE 140, 240, 340 to define a second part of the interaction volume 114, to intercept the attenuated energy 112 along a plurality of path lengths, and to substantially simultaneously transform the attenuated energy 112 characterized by a substantially exponential intensity function into resultant energy 118 characterized by a substantially polynomial intensity function. The substantially polynomial intensity function may take the form $A(m)*X^{(-m)}+A(-m+n)*X^{(-m+n)} \ldots A(m+n)*X^{(m+n)}+A(m)*X^{(m)}$, where m and n can be real or imaginary.

Thus, the apparatus 100, 200, 300 may comprise a chamber 290 bounded at least partially by an IETE 140, 240, 340. Potential embodiments of chambers 290 include flow cells and cuvettes, among others. The incident energy 108 includes "light" energy as electromagnetic radiation characterized by one or more frequencies having a wavelength within a range of about 10 nanometers to about 100 micrometers. The incident energy 108 also includes other wavelengths and types of energy.

Derivation of the polynomial intensity function has been described previously. The polynomial intensity function may comprise a substantially linear approximation (e.g., linear or substantially parabolic).

The IETE 140, 240, 340 intercepts the attenuated energy 112 at an entrance surface 120. The exit surface 122 of the IETE 140, 240, 340 defines the end of each path along which the attenuated energy 112 travels as it is transformed by the element 140, 240, 340, at which point it becomes resultant energy 118. Thus, the attenuated energy 112 can be substantially simultaneously transformed along the plurality of path lengths 116 so as to be characterized by the substantially polynomial intensity function at ends of the plurality of path lengths 116 defined by an exit surface 122 of the IETE 140, 240, 340. As noted previously, the incident/attenuated energy may comprises a variety of energy types, including light, as well as one or more of electromagnetic energy, acoustic energy (e.g., comprising neutrons, electricity, or semiconductor phonons), or particle energy.

The IETE 140, 240, 340 may comprise a number of materials, including one or more of polymers, crystalline materials, and amorphous materials (e.g., glass), as well as homogeneous and heterogenous materials. While the interaction volume 114 may be adjustable, it can also comprise a fixed, non-adjustable volume (as shown in FIG. 2), including a fluid sampling volume.

The IETE 140, 240, 340 may be constructed to have a variety of transformation characteristics. For example, the IETE 140, 240, 340 may be constructed so that the wavelength-dependent total intensity (or inverse of total intensity) of the intercepted, attenuated energy 112 is transformed to have a substantially linear relationship to the wavelength-dependent optical density of the material sample. Thus, the IETE 140, 240, 340 may define the interaction volume 114 to intercept a wavelength-dependent total intensity of the attenuated energy 112 associated with a material sample 230 located in the interaction volume 114, the total intensity or an inverse of the total intensity being substantially linear with respect to a wavelength-dependent optical density of the material sample 230.

In some embodiments, the IETE 140, 240, 340 may be constructed to define the interaction volume 114 so as to intercept attenuated energy 112 characterized by the substantially exponential intensity function comprising a wavelength-dependent total intensity function. That is, the attenuated energy 112 can sometimes be characterized by an exponential total intensity function that is wavelength-dependent. The attenuation of the attenuated energy 112 can be measured as optical density with respect to a wavelength of electromagnetic energy in some embodiments. The electromagnetic energy may include energy ranging from microwaves (about $10^{-1}$ m wavelength) to gamma rays (about $10^{-12}$ m wavelength).

Energy transformation can occur over a range of sample material optical density that varies by an order of magnitude, or more, on up to several orders of magnitude. Thus, the IETE 140, 240, 340 may operate to transform the attenuated energy 112 from a substantially exponential intensity to a substantially linear intensity over a range of optical density associated with a sample material in the interaction volume that is at least 10:1. The sample material optical density transformation range may even be significantly greater, such as more than 64:1 or even more than 128:1. The term "linear" in this case includes linearity with respect to coefficients of independent variables in a matrix, as used by those of ordinary skill in the field of matrix algebra.

The IETE 140, 240, 340 may be realized using a variety of physical embodiments. For example, the IETE 140, 240, 340 may be fabricated by machining a crystal, such as sapphire, or by joining together a bundle of glass fibers. Thus, the IETE 140, 240, 340 may comprise one of a substantially homogeneous material or a bundle of optically conducting fibers. The ends of an optical fiber bundle may be used to form the incident face 120, 320 of the IETE 140, 240, 340, which is the face that serves to intercept the attenuated energy 112. Thus, the incident face 120, 320 of the IETE 140, 240, 340 can be formed using ends of a bundle of optically conducting fibers. The fibers may be arranged to form a non-smooth, discontinuous, incident face (e.g., see element 312 in FIG. 3). Thus, the incident face 120, 320 may comprise a substantially discontinuous arrangement of the ends of the fibers. In some embodiments, the IETE 140, 240, 340 comprises a bundle of coherent light conducting fibers.

A number of geometric shapes can be used to define the incident face 120, 320 of the IETE 140, 240, 340. For example, the incident face 120, 320 of the element 140, 240, 340 may comprise at least a portion of a stepwise-continuous surface, a substantially spherical surface, a substantially planar surface, a substantially conical surface, a substantially parabolic surface, or a substantially logarithmic surface, among others.

The incident face 120, 320 may be parallel to (as shown in FIGS. 1 and 2) or perpendicular to sampled material flowing through the interaction volume 114. Thus, the incident face 120, 320 of the element 140, 240, 340 may be substantially parallel or substantially orthogonal to a fluid flow path defined, at least in part, by the chamber 290. If orthogonal, for example, the fluid may be sprayed or formed as a jet to impinge directly against the face 120, 320 perhaps following the incident energy 108, 208 along the optical path 228 after passing through one or more apertures in the window 224.

Some embodiments provide diverging paths for the attenuated energy 112 caused by multiple elements 240 defining the interaction volume, such as when a triangular chamber is created within a tubular window (as shown for apparatus 200'' in FIG. 2). Thus, the plurality of paths 116 may be divided into two or more parts 286, a first one of the parts 286 impinging on an incident face of the transformation element 240, and a second one of the parts 286 impinging on another incident face of another transformation element 240.

In some embodiments, the apparatus 200 may comprise one or more receivers 250, such as a photodetector. The receiver 250 can be included as a way to integrate the multiple path lengths 116 at the same time. Thus, the receiver 250 may operate to receive the resultant energy 118 after the resultant energy 118 exits the element 140, 240.

An aspheric back end may be located within the chamber 290, perhaps mounted or molded to a window 124 defined by an interior surface of the chamber 290. Thus, an aspheric correction element 126 may be disposed between an interior surface of the chamber 290 and an incident face 120, 320 of the element 140, 240, 340. Still further embodiments may be realized.

For example, a system 202 may comprise a source 212 of incident energy 108, 208 and a receiver 250, as well as a chamber 290 and an IETE 140, 240, 340 described previously.

In some embodiments, the chamber may be substantially prismatic (e.g., see apparatus 200'' in FIG. 2). The interaction volume may be partially or completely defined by three partial cylinders implemented as windows 244 disposed around the chamber 290.

The embodiments described may be changed to accommodate a variety of analysis characteristics. For example, the source 212 may comprise a number of types of sources, including a tunable frequency light source or a fixed frequency source, such as a laser. The system 202 may include one or more parabolic reflectors 260 to substantially re-collimate the energy after it passes through the element 140, 240. Thus, the system 202 may comprise at least a portion of a substantially parabolic reflector 260 disposed between the IETE 140, 240 and the receiver 250 along the optical path of the resultant energy 118 (see apparatus 200'').

The system 202 may further comprise a housing 294, such as a down hole tool or tool body that is attached to include any one or more of the components shown in FIGS. 1-3. Thus, the system 202 can form part of a subsurface exploration system, with a down hole tool used to house the source 212, the receiver 250, and the chamber 290.

Figure 4:
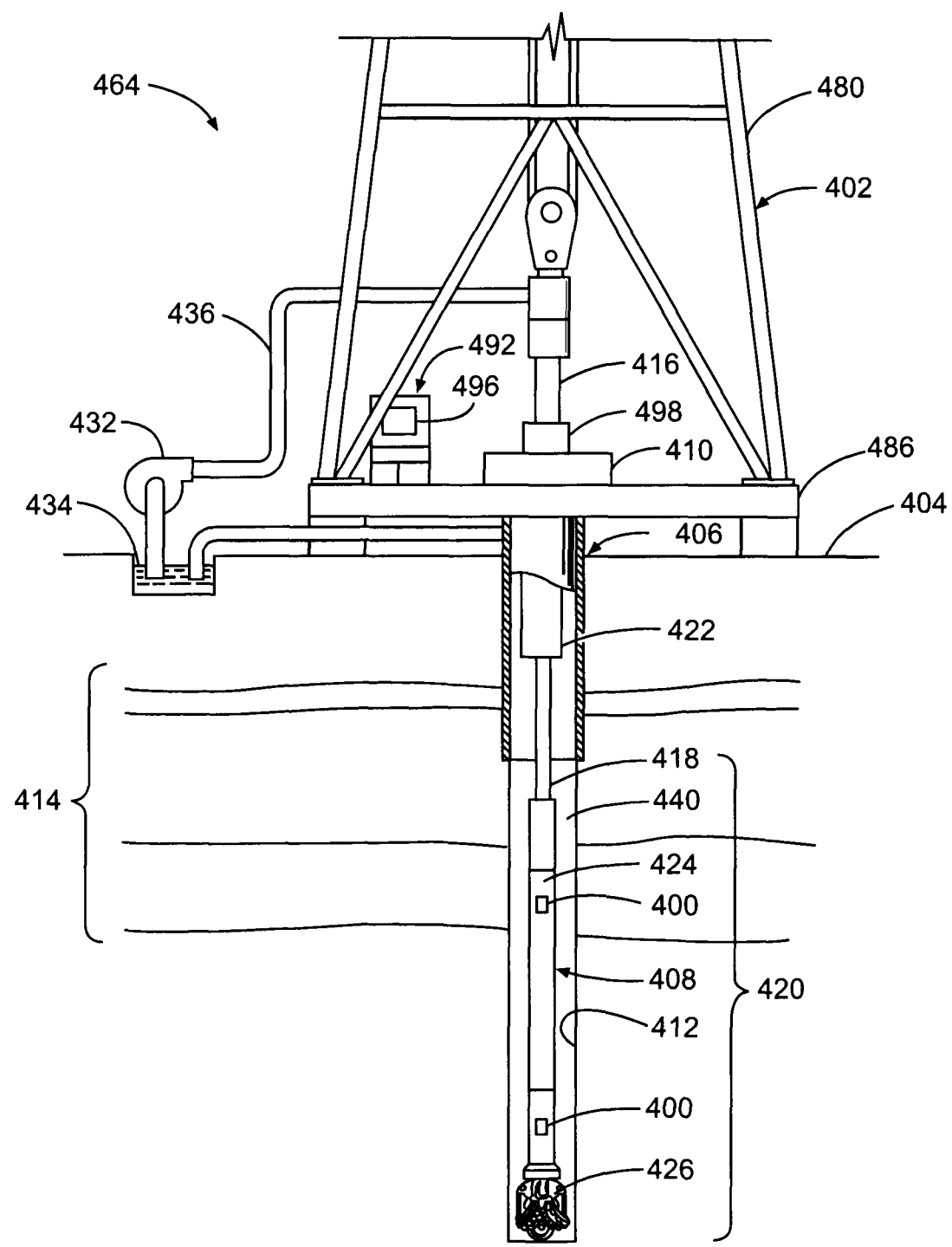
FIGS. 4-5 illustrate additional system embodiments of the invention.
Figure 5:
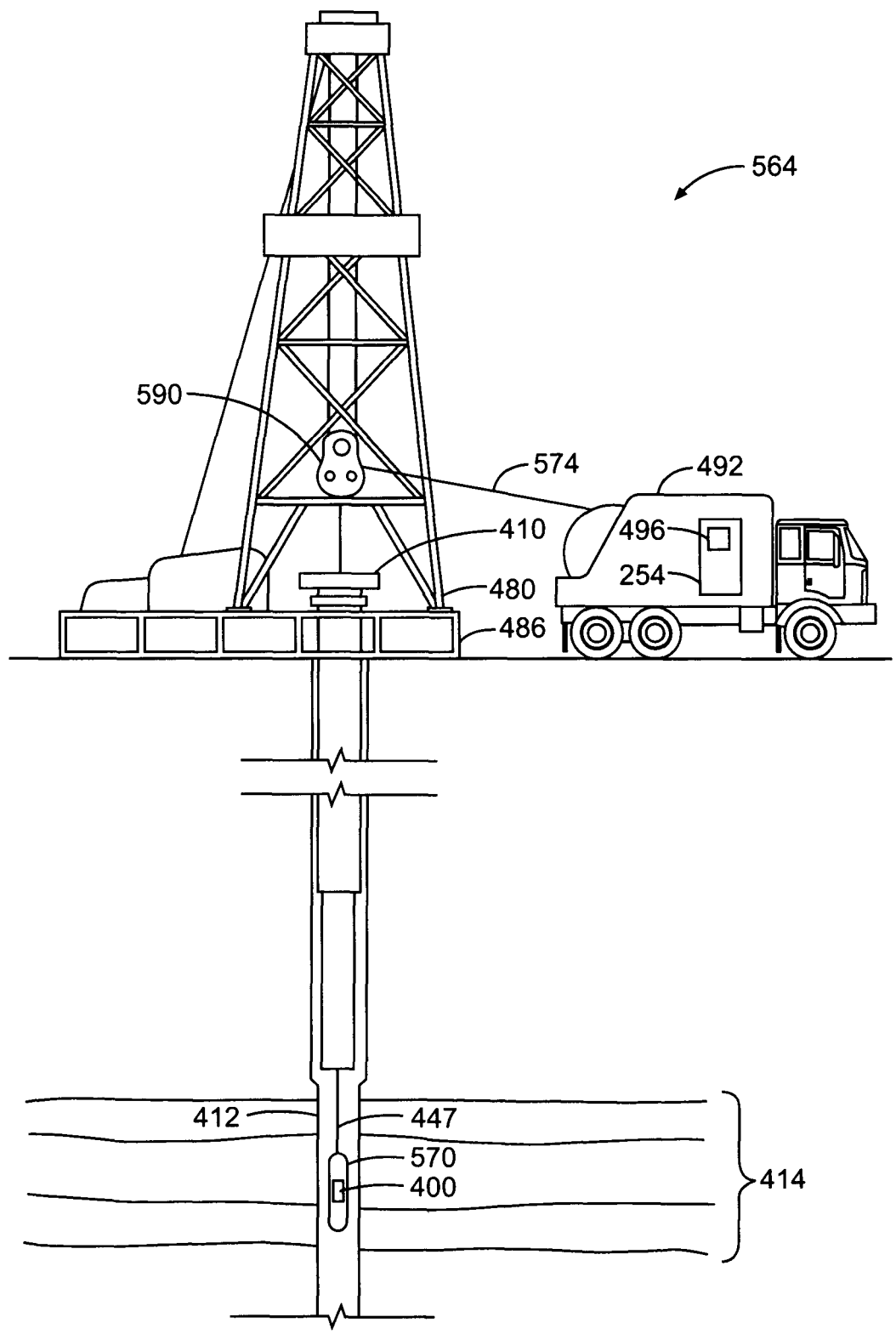

FIGS. 4-5 illustrate additional system embodiments of the invention. For example, FIG. 4 illustrates a system 464 as a drilling rig system embodiment of the invention, and FIG. 5 illustrates a system 564 as a wireline system embodiment of the invention. Thus, systems 464, 564 may comprise portions of a down hole tool 424 as part of a down hole drilling operation, or a tool body 570 as part of a wireline logging operation.

Drilling of oil and gas wells is commonly carried out using a string of drill pipes connected together so as to form a drilling string that is lowered through a rotary table 410 into a wellbore or borehole 412. Turning now to FIG. 4, it can be seen how a system 464 may form a portion of a drilling rig 402 located at the surface 404 of a well 406. The drilling rig 402 may provide support for a drill string 408. The drill string 408 may operate to penetrate a rotary table 410 for drilling a borehole 412 through subsurface formations 414. The drill string 408 may include a Kelly 416, drill pipe 418, and a bottom hole assembly 420, perhaps located at the lower portion of the drill pipe 418. In some embodiments, one or more instruments 400, similar to or identical to the system 202 of FIG. 2, may be carried and thus attached to the drill string 408 or the down hole tool 424.

The bottom hole assembly 420 may include drill collars 422, a down hole tool 424, and a drill bit 426. The drill bit 426 may operate to create a borehole 412 by penetrating the surface 404 and subsurface formations 414. The down hole tool 424 may comprise any of a number of different types of tools including MWD (measurement while drilling) tools, LWD (logging while drilling) tools, and others.

During drilling operations, the drill string 408 (perhaps including the Kelly 416, the drill pipe 418, and the bottom hole assembly 420) may be rotated by the rotary table 410. In addition to, or alternatively, the bottom hole assembly 420 may also be rotated by a motor (e.g., a mud motor) that is located down hole. The drill collars 422 may be used to add weight to the drill bit 426. The drill collars 422 may also operate to stiffen the bottom hole assembly 420, allowing the bottom hole assembly 420 to transfer the added weight to the drill bit 426, and in turn, to assist the drill bit 426 in penetrating the surface 404 and subsurface formations 414.

During drilling operations, a mud pump 432 may pump drilling fluid (sometimes known by those of skill in the art as "drilling mud") from a mud pit 434 through a hose 436 into the drill pipe 418 and down to the drill bit 426. The drilling fluid can flow out from the drill bit 426 and be returned to the surface 404 through an annular area 440 between the drill pipe 418 and the sides of the borehole 412. The drilling fluid may then be returned to the mud pit 434, where such fluid is filtered. In some embodiments, the drilling fluid can be used to cool the drill bit 426, as well as to provide lubrication for the drill bit 426 during drilling operations. Additionally, the drilling fluid may be used to remove subsurface formation 414 cuttings created by operating the drill bit 426.

FIG. 5 shows a well during wireline logging operations. A drilling platform 486 is equipped with a derrick 480 that supports a hoist 590. Here it is assumed that the drilling string has been temporarily removed from the borehole 412 to allow a wireline logging tool body 570, such as a probe or sonde that carries one or more instruments 400, to be lowered by wireline or logging cable 574 into the borehole 412. Typically, the tool body 570 is lowered to the bottom of the region of interest and subsequently pulled upward at a substantially constant speed.

During the upward trip, the instruments 400 included in the tool body 470 may be used to perform measurements in the borehole 412 as they pass by. In some formation evaluation tools, the tool body 470 may be stopped, a probe extended, and a sample of fluid pumped from the formation. Within the tool body 470 the fluid properties may be measured before being sampled or returned to the well bore. The tool body 470 may comprise some portion of the housing 294 of FIG. 2. The measurement data can be communicated to a surface logging facility 492 for storage, processing, and analysis. The logging facility 492 may be provided with electronic equipment, such as a processor and any one or more of the components of the system 202 in FIG. 2. The measurement data may include data similar to that which is gathered and analyzed during drilling operations (e.g., during LWD operations).

The systems 400, 464 of FIGS. 4 and 5 may comprise a display 496. The display 494 may be used to display the measurement data, perhaps including data derived from a signal provided by the receiver (e.g., the signal 252 of the receiver 250 in FIG. 2). Such data may include derived data, including the optical density of the sampled material disposed in the interaction volume of the apparatus 100, 200, 300 of FIGS. 1, 2, and 3, respectively.

The apparatus 100, 200, 300; cross section 104; energy 108, 208; attenuated energy 112; interaction volume 114; paths 116; resultant energy 118; incident surfaces 120, 320; exit surface 122; correction element 126; IETE 140, 240, 340; energy source 212; reflectors 216, 260; slit 220; windows 224, 244; optical axis 228; sample 230; IETE 140, 240; optics 242; receiver 250; signal 252; tube 284; parts 286; chamber 290; beams 292; element 312; instrument 400; drilling rig 402; well 406; drill string 408; rotary table 410; borehole 412; formation 414; Kelly 416; drill pipe 418; bottom hole assembly 420; drill collars 422; down hole tool 424; drill bit 426; mud pump 432; mud pit 434; hose 436 systems 464, 564; tool body 470; drilling platform 486; derrick 480; logging facility 492; display 496; logging cable 574; and hoist 590 may all be characterized as "modules" herein. Such modules may include hardware circuitry, and/or a processor and/or memory circuits, software program modules and objects, and/or firmware, and combinations thereof, as desired by the architect of the apparatus 100, 200, 300; instruments 400; and systems 202, 464, 564, and as appropriate for particular implementations of various embodiments. For example, in some embodiments, such modules may be included in an apparatus and/or system operation simulation package, such as a software electrical signal simulation package, a power usage and distribution simulation package, a power/heat dissipation simulation package, and/or a combination of software and hardware used to simulate the operation of various potential embodiments.

It should also be understood that the apparatus and systems of various embodiments can be used in applications other than for logging operations, and thus, various embodiments are not to be so limited. The illustrations of apparatus 100, 200, 300; instruments 400; and systems 202, 464, 564 are intended to provide a general understanding of the structure of various embodiments, and they are not intended to serve as a complete description of all the elements and features of apparatus and systems that might make use of the structures described herein.

Applications that may incorporate the novel apparatus and systems of various embodiments include a variety of electronic systems, such as televisions, cellular telephones, personal computers, workstations, radios, video players, vehicles, portable devices containing acceleration sensors (ie. certain cellular telephones and PDAs) and location technology (e.g., GPS (Global Positioning System) location technology), signal processing for geothermal tools and smart transducer interface node telemetry systems, among others. Some embodiments include a number of methods.

Figure 6:
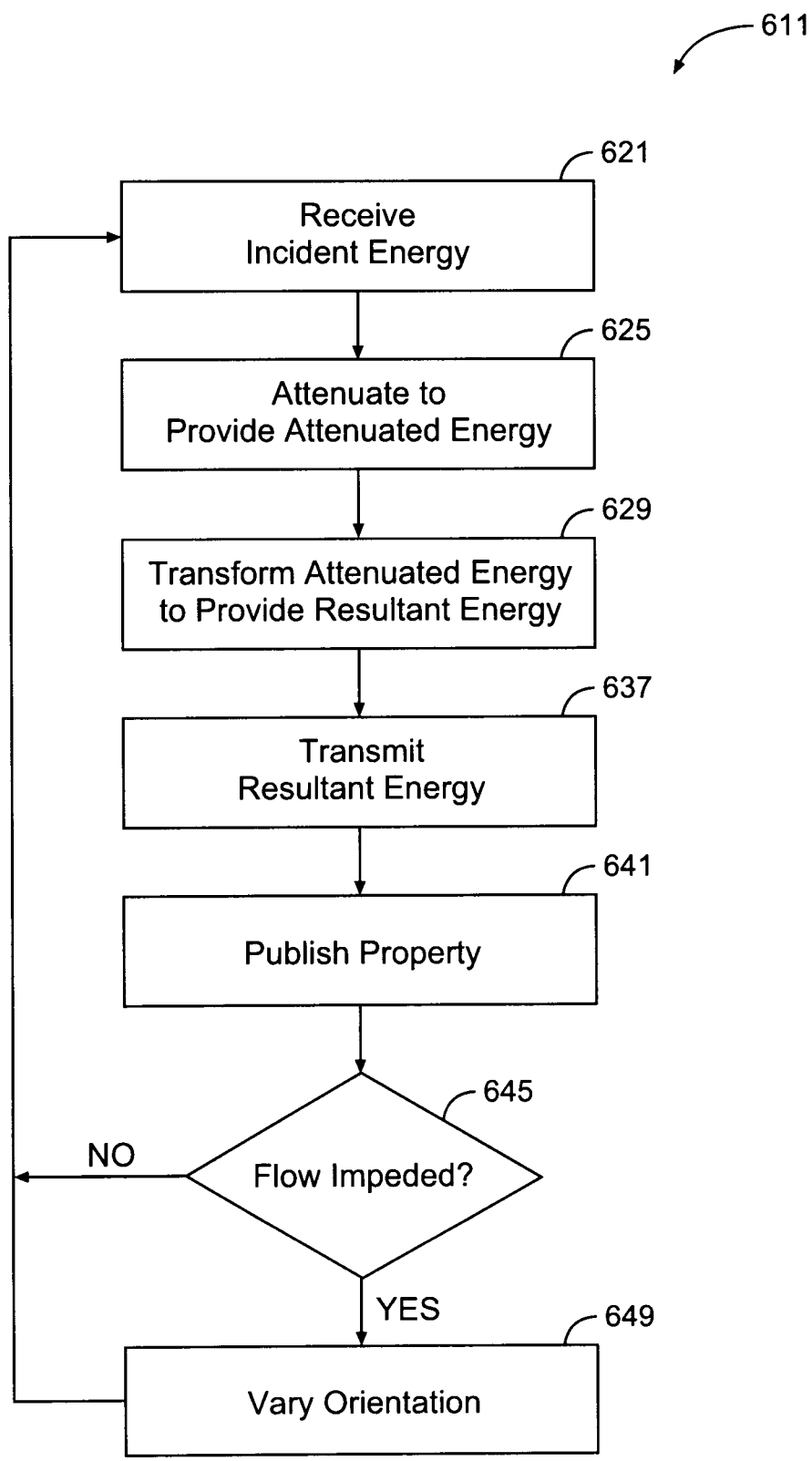
FIG. 6 is a flow chart illustrating several methods according to various embodiments of the invention.

FIG. 6 is a flow chart illustrating several methods according to various embodiments of the invention. For example, a processor-implemented method 611 to execute on one or more processors that perform the method to transform incident energy as described previously may begin at block 621 with receiving incident energy within a chamber defining a first part of an interaction volume. The activity of receiving at block 621 may further comprise receiving the attenuated energy at an incident face of the transformation element comprising a plurality of stepwise-continuous surfaces, among others.

The method 611 may continue on to block 625 with using the interaction volume, perhaps containing a sampled material, to attenuate the incident energy as a function of path length to provide attenuated energy after the incident energy has traveled through the interaction volume along a plurality of paths.

The method 611 may continue on to block 629 to include (substantially simultaneously) transforming the attenuated energy characterized by a substantially exponential intensity function into resultant energy. The resultant energy may be characterized by a substantially polynomial intensity function. The transformation may be accomplished using an interacted energy transformation element that defines a second part of the interaction volume, the transformation element operating to intercept the attenuated energy along a plurality of path lengths corresponding to the plurality of paths.

The two-dimensional point path length across the interaction volume may be defined according to a logarithmic function. Thus, a distance t across the interaction volume from an interior surface of the chamber to an incident surface of the transformation element can be approximated as $1-\ln(x)$ for at least one cross-section of the interaction volume.

The transformation element can be designed to provide a selectable dynamic range. Thus, in some embodiments, the transformation operates to increase the effective dynamic range of the receiver.

The method 611 may continue on to block 637 to include transmitting the resultant energy to a receiver. The resultant energy can be collimated or otherwise modified after transformation, to accommodate "beam-walk", as noted previously, perhaps using one or more parabolic reflectors. Thus, activity of transmitting at block 637 may further comprise re-collimating the resultant energy after the resultant energy passes through the transformation element, and before the resultant energy impinges on the receiver.

The material properties of a sample can be determined based on the received intensity of the resultant energy, and published to a display, memory, or printer. Thus, the method 611 may continue on to block 641 to include publishing a material property or a chemical property of a sample material disposed in the interaction volume based on intensity of the resultant energy as determined at the receiver.

If the material that is sampled includes a fluid flow, such as the flow of oil in a sampling chamber, the method 611 may continue on to include determining whether the flow has been impeded, perhaps by the buildup of particles within the chamber at block 645. If not, the method 611 may continue on to bock 621.

If the flow of fluid to be sampled has been impeded (e.g., perhaps as defined by a drop in pressure within the chamber, or a drop in fluid flow velocity), as determined at block 645, the method 611 may continue on to block 649, to include varying the orientation of the incident face of the transformation element with respect to the flow of sampled material through the interaction volume. Moving the incident or entrance face of the transformation element may serve to dislodge the substance impeding the flow.

It should be noted that the methods described herein do not have to be executed in the order described, or in any particular order. Moreover, various activities described with respect to the methods identified herein can be executed in iterative, serial, or parallel fashion. Some activities may be added, and some of the included activities may be left out. Information, including parameters, commands, operands, and other data, can be sent and received in the form of one or more carrier waves.

Figure 7:
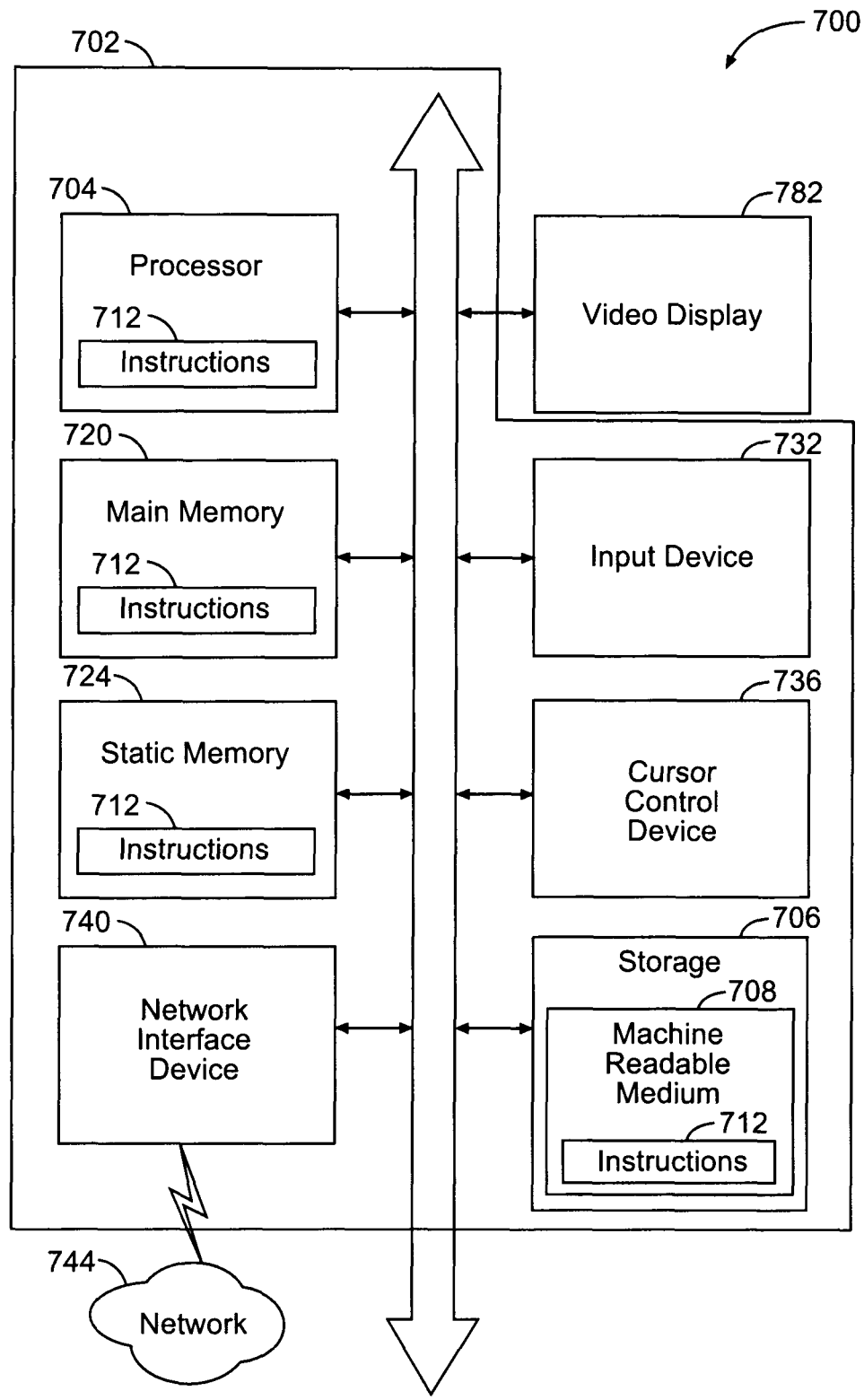
FIG. 7 is a block diagram of an article according to various embodiments of the invention.
Figure 8:
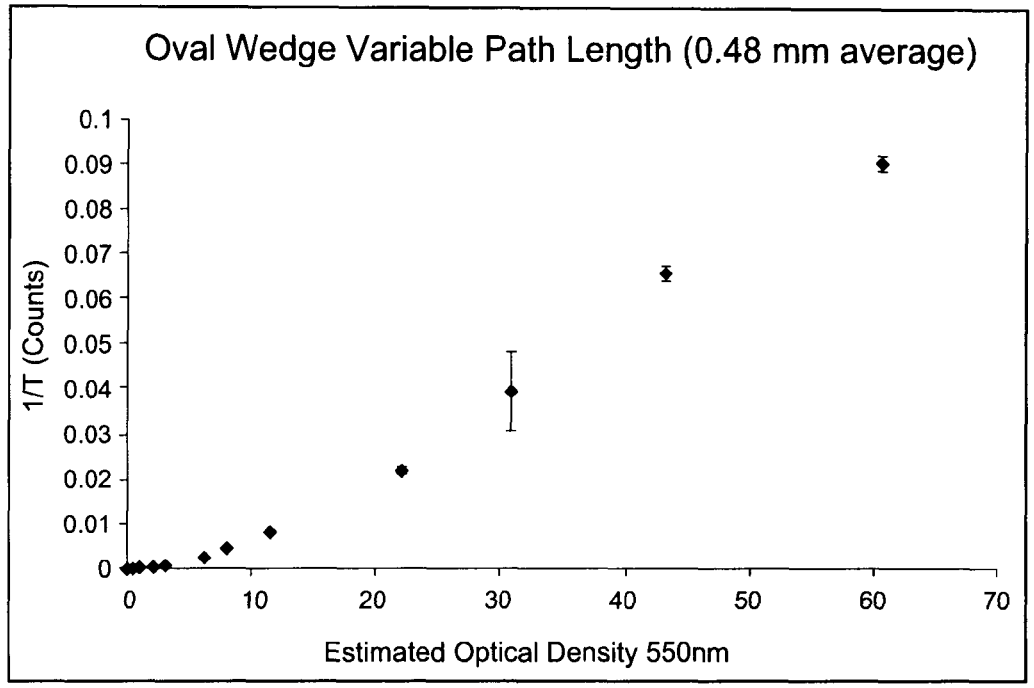
FIGS. 8-14 are plots of experimental data results according to various embodiments of the invention.
Figure 9:
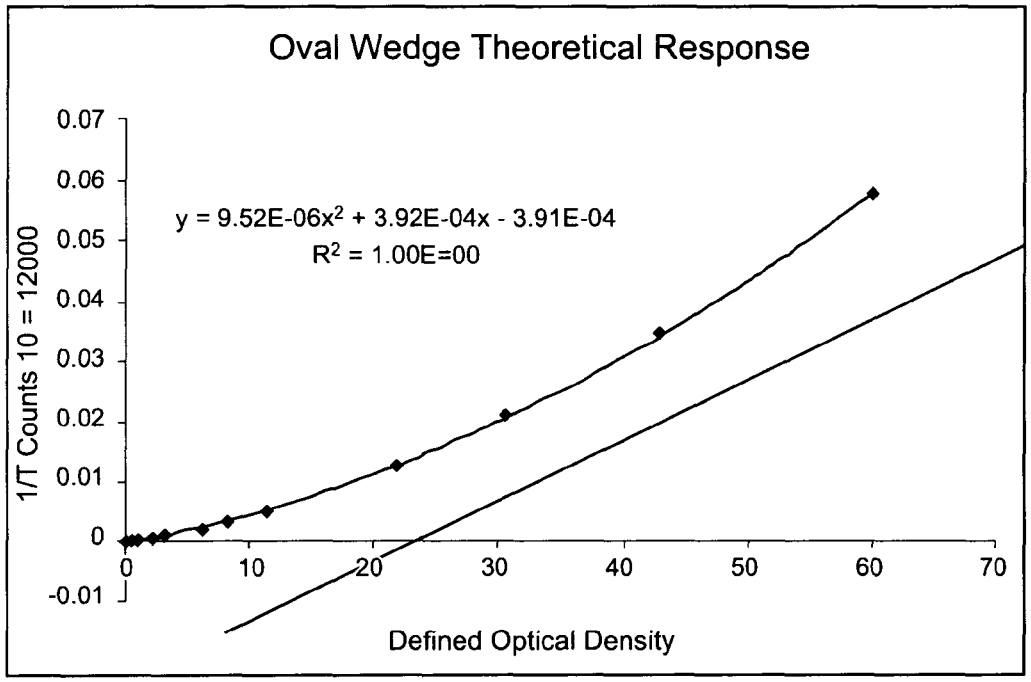
Figure 10:
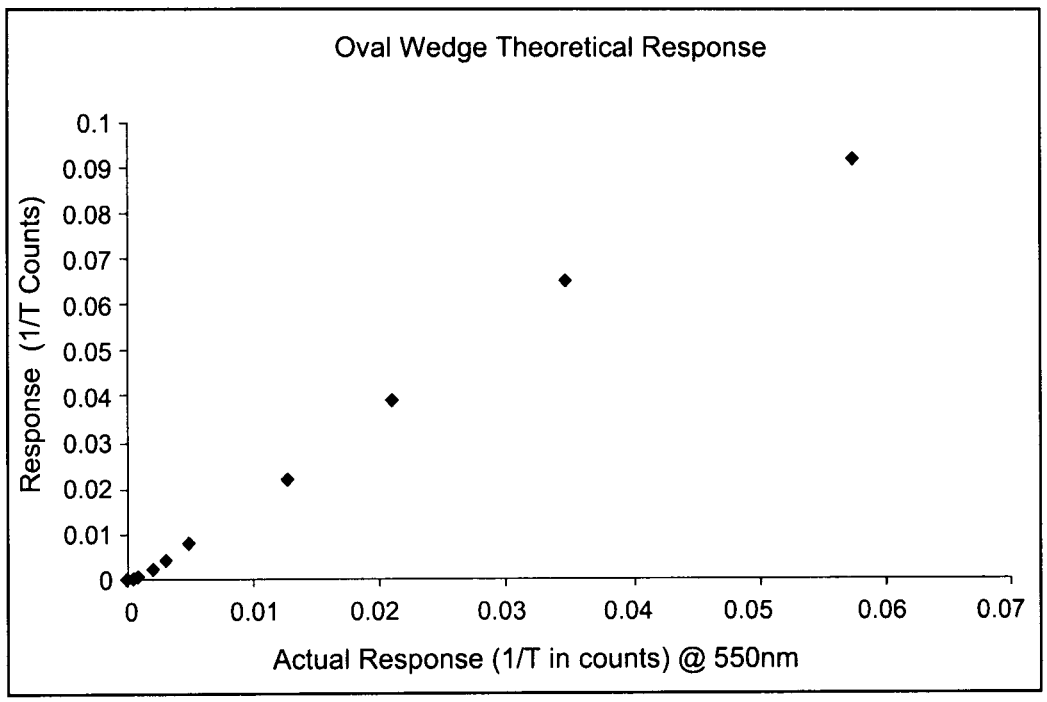
Figure 11:
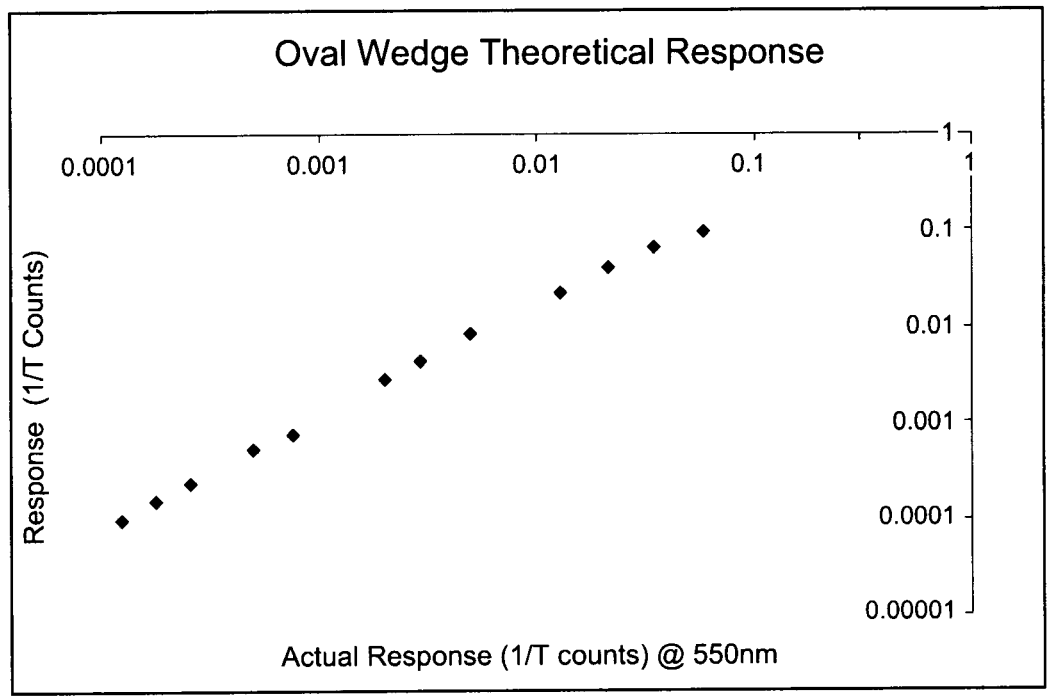
Figure 12:
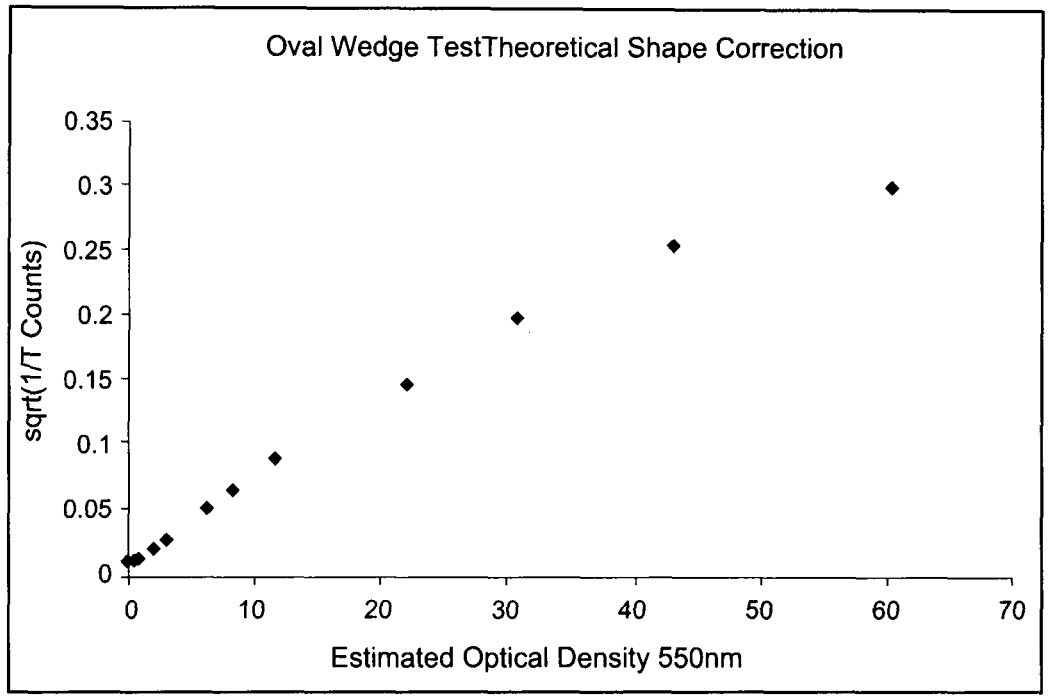
Figure 13:
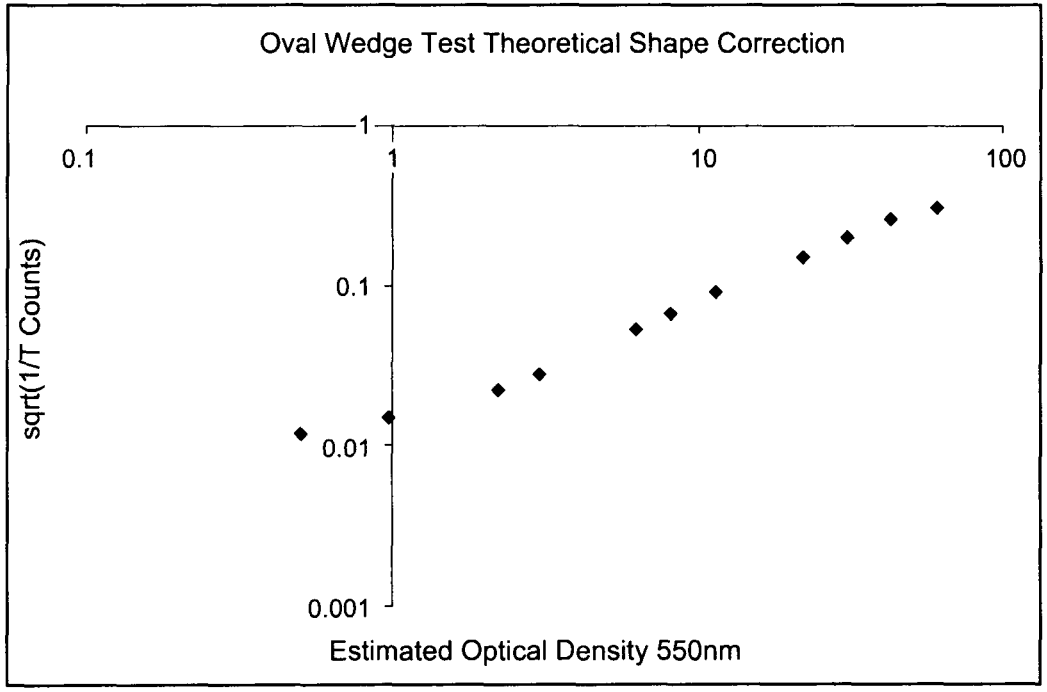
Figure 14:
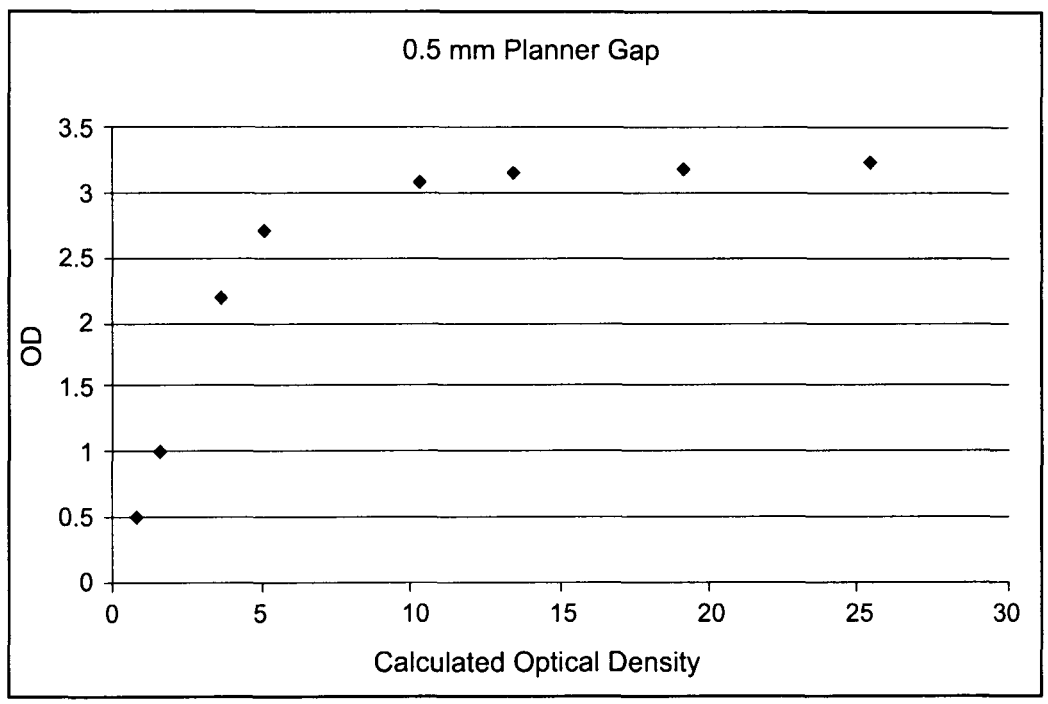

FIG. 7 is a block diagram of an article 700 of manufacture, including a specific machine 702, according to various embodiments of the invention. Upon reading and comprehending the content of this disclosure, one of ordinary skill in the art will understand the manner in which a software program can be launched from a computer-readable medium in a computer-based system to execute the functions defined in the software program.

One of ordinary skill in the art will further understand the various programming languages that may be employed to create one or more software programs designed to implement and perform the methods disclosed herein. The programs may be structured in an object-orientated format using an object-oriented language such as Java or C++. Alternatively, the programs can be structured in a procedure-orientated format using a procedural language, such as assembly or C. The software components may communicate using any of a number of mechanisms well known to those of ordinary skill in the art, such as application program interfaces or interprocess communication techniques, including remote procedure calls. The teachings of various embodiments are not limited to any particular programming language or environment. Thus, other embodiments may be realized.

For example, an article 700 of manufacture, such as a computer, a memory system, a magnetic or optical disk, some other storage device, and/or any type of electronic device or system may include one or more processors 704 coupled to a machine-readable medium 708 such as a memory (e.g., removable storage media, as well as any memory including an electrical, optical, or electromagnetic conductor comprising tangible media) having instructions 712 stored thereon (e.g., computer program instructions), which when executed by the one or more processors 704 result in the machine 702 performing any of the actions described with respect to the processes or methods described above.

The machine 702 may take the form of a specific computer system having a processor 704 coupled to a number of components directly, and/or using a bus 716. Thus, the machine 702 may be similar to or identical to the logging facility 492 shown in FIGS. 4 and 5.

Turning now to FIG. 7, it can be seen that the components of the machine 702 may include main memory 720, static or non-volatile memory 724, and mass storage 706. Other components coupled to the processor 704 may include an input device 732, such as a keyboard, or a cursor control device 736, such as a mouse. An output device 728, such as a video display, may be located apart from the machine 702 (as shown), or made as an integral part of the machine 702.

A network interface device 740 to couple the processor 704 and other components to a network 744 may also be coupled to the bus 716. The instructions 712 may be transmitted or received over the network 744 via the network interface device 740 utilizing any one of a number of well-known transfer protocols (e.g., HyperText Transfer Protocol). Any of these elements coupled to the bus 716 may be absent, present singly, or present in plural numbers, depending on the specific embodiment to be realized.

The processor 704, the memories 720, 724, and the storage device 706 may each include instructions 712 which, when executed, cause the machine 702 to perform any one or more of the methodologies described herein. In some embodiments, the machine 702 operates as a standalone device or may be connected (e.g., networked) to other machines. In a networked environment, the machine 702 may operate in the capacity of a server or a client machine in server-client network environment, or as a peer machine in a peer-to-peer (or distributed) network environment.

The machine 702 may comprise a personal computer (PC), a workstation, a tablet PC, a set-top box (STB), a PDA, a cellular telephone, a web appliance, a network router, switch or bridge, server, client, or any specific machine capable of executing a set of instructions (sequential or otherwise) that direct actions to be taken by that machine to implement the methods and functions described herein. Further, while only a single machine 702 is illustrated, the term "machine" shall also be taken to include any collection of machines that individually or jointly execute a set (or multiple sets) of instructions to perform any one or more of the methodologies discussed herein.

While the machine-readable medium 708 is shown as a single medium, the term "machine-readable medium" should be taken to include a single medium or multiple media (e.g., a centralized or distributed database, and/or associated caches and servers, and or a variety of storage media, such as the registers of the processor 704, memories 720, 724, and the storage device 706 that store the one or more sets of instructions 712. The term "machine-readable medium" shall also be taken to include any medium that is capable of storing, encoding or carrying a set of instructions for execution by the machine and that cause the machine 702 to perform any one or more of the methodologies of the present invention, or that is capable of storing, encoding or carrying data structures utilized by or associated with such a set of instructions. The terms "machine-readable medium" or "computer-readable medium" shall accordingly be taken to include tangible media, such as solid-state memories and optical and magnetic media.

Various embodiments may be implemented as a stand-alone application (e.g., without any network capabilities), a client-server application or a peer-to-peer (or distributed) application. Embodiments may also, for example, be deployed by Software-as-a-Service (SaaS), an Application Service Provider (ASP), or utility computing providers, in addition to being sold or licensed via traditional channels.

Using the apparatus, systems, and methods disclosed, those in the petroleum recovery industry and other industries may now be able to extend the range of optical densities for analyzed samples in comparison to the more conventional fixed path length cell, perhaps by several orders of magnitude. Additional benefits may include reducing the dynamic range demands on available detectors, and performing a wavelength-dependent logarithmic transform on attenuated light such that the output optical density as a function of wavelength is proportional to chemical and physical-chemical sample information.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An apparatus, comprising:
a chamber to define a first part of an interaction volume that attenuates incident energy as a function of path length to provide attenuated energy after the incident energy has traveled through the interaction volume along a plurality of paths; and
an interacted energy transformation element to define a second part of the interaction volume, to intercept the attenuated energy along a plurality of path lengths, and to substantially simultaneously transform the attenuated energy characterized by a substantially exponential intensity function into resultant energy characterized by a substantially polynomial intensity function.

2. The apparatus of claim 1, wherein the attenuated energy is substantially simultaneously transformed along the plurality of path lengths so as to be characterized by the substantially polynomial intensity function at ends of the plurality of path lengths defined by an exit surface of the transformation element.

3. The apparatus of claim 1, wherein the attenuated energy comprises at least one of electromagnetic energy, acoustic energy comprising at least one of neutrons, electricity, or semiconductor phonons, or particle energy.

4. The apparatus of claim 1, wherein the transformation element comprises one of a crystalline material or an amorphous material.

5. The apparatus of claim 1, wherein the interaction volume comprises a fixed, non-adjustable fluid sampling volume.

6. The apparatus of claim 1, wherein the transformation element defines the interaction volume to intercept a wavelength-dependent total intensity of the attenuated energy associated with a material sample located in the interaction volume, the total intensity or an inverse of the total intensity being substantially linear with respect to a wavelength-dependent optical density of the material sample.

7. The apparatus of claim 1, wherein attenuation of the attenuated energy can be measured as optical density with respect to a wavelength of electromagnetic energy.

8. The apparatus of claim 1, wherein the transformation element defines the interaction volume so as to intercept the attenuated energy characterized by a substantially exponential total intensity function that is wavelength-dependent.

9. The apparatus of claim 1, wherein the transformation element comprises:
one of a substantially homogeneous material, a substantially heterogeneous material, or a bundle of optically conducting fibers.

10. The apparatus of claim 1, wherein an incident face of the transformation element comprises at least a portion of one of a substantially discontinuous arrangement of optically conducting fiber ends, a stepwise-continuous surface, a substantially spherical surface, a substantially planar surface, a substantially conical surface, a substantially parabolic surface, or a substantially logarithmic surface.

11. The apparatus of claim 1, wherein an incident face of the transformation element is one of substantially parallel or substantially orthogonal to a fluid flow path defined, at least in part, by the chamber.

12. The apparatus of claim 1, wherein the plurality of paths are divided into at least two parts, a first one of the parts impinging on an incident face of the transformation element, and a second one of the parts impinging on another incident face of another transformation element.

13. The apparatus of claim 1, further comprising:
at least one of a source to provide the incident energy or a receiver to receive the resultant energy.

14. The apparatus of claim 1, further comprising:
an aspheric correction element disposed between an interior surface of the chamber and an incident face of the transformation element.

15. The apparatus of claim 1, wherein the chamber is substantially prismatic, and wherein the interaction volume is at least partially defined by three partial cylinders disposed around the chamber.

16. The apparatus of claim 1, further comprising:
a down hole tool to house the chamber.

17. A method, comprising:
receiving incident energy within a chamber defining a first part of an interaction volume that attenuates the incident energy as a function of path length to provide attenuated energy after the incident energy has traveled through the interaction volume along a plurality of paths;
substantially simultaneously transforming the attenuated energy characterized by a substantially exponential intensity function into resultant energy characterized by a substantially polynomial intensity function using an interacted energy transformation element that defines a second part of the interaction volume, the transformation element operating to intercept the attenuated energy along a plurality of path lengths corresponding to the plurality of paths; and
transmitting the resultant energy to a receiver.

18. The apparatus of claim 1, wherein a distance y across the interaction volume from an interior surface of the chamber to an incident surface of the transformation element is approximated as $1-\ln(x)$ for at least one cross-section of the interaction volume.

19. The method of claim 17, further comprising:
publishing a material property or a chemical property of a sample material disposed in the interaction volume based on intensity of the resultant energy as determined at the receiver.

20. The method of claim 17, wherein the receiving further comprises:
receiving the attenuated energy at an incident face of the transformation element comprising a plurality of stepwise-continuous surfaces.

* * * * *